US00PP10288P

United States Patent [19]

Enthoven

[11] Patent Number: Plant 10,288

[45] Date of Patent: Mar. 17, 1998

[54] GERANIUM PLANT NAMED 'MERIFESTIVAL'

[75] Inventor: Adrianus W. M. Enthoven, Wateringen, Netherlands

[73] Assignee: Enthoven Breeding B.V., Wateringen, Netherlands

[21] Appl. No.: 764,391

[22] Filed: Dec. 13, 1996

[51] Int. Cl.[6] ..... A01H 5/00

[52] U.S. Cl. ..... Plt./87.12

[58] Field of Search ..... Plt./87.12

*Primary Examiner*—James R. Feyrer
*Attorney, Agent, or Firm*—C. A. Whealy

[57] ABSTRACT

A new and distinct cultivar of Geranium plant named 'Merifestival', characterized by its rounded upright growth habit; moderate growth rate and vigor; freely branching plant habit; fast rooting; medium green foliage color; numerous peduncles with four to six flowers per umbel; large double lilac flowers; and good weather and stress tolerance.

2 Drawing Sheets

The present invention relates to a new and distinct cultivar of Geranium plant, botanically known as *Pelargonium× peltatum*, and hereinafter referred to by the cultivar name Merifestival.

The new cultivar is a product of a planned breeding program conducted by the inventor in Wateringen, The Netherlands. The objective of the breeding program was to develop new ivy Geranium cultivars with double or semi-double flowers, fast rooting, tolerance to Botrytis, weather resistance, many peduncles with few flowers, compact and pendant growth habit, and interesting and unique flower colors.

The new cultivar originated from a cross made by the inventor of two unidentified proprietary seedling selections. The cultivar 'Merifestival' was discovered and selected by the inventor as a flowering plant within the progeny of the stated cross in a controlled environment in Wateringen, The Netherlands, in June, 1992.

Compared to plants of the seed parent, plants of the new cultivar are lighter in flower color. Compared to plants of the pollen parent, plants of the new cultivar are darker in flower color.

Asexual reproduction of the new cultivar by terminal cuttings taken at Wateringen, The Netherlands, has shown that the unique features of this new Geranium are stable and reproduced true to type in successive generations of asexual reproduction.

The following traits have been repeatedly observed and are determined to be the unique characteristics of 'Merifestival'. These characteristics in combination distinguish 'Merifestival' as a new and distinct cultivar:

1. Rounded upright growth habit.
2. Moderate growth rate and vigor.
3. Freely branching plant habit.
4. Fast rooting.
5. Medium green foliage color.
6. Numerous peduncles with four to six flowers per umbel.
7. Large double lilac flowers.
8. Good weather and stress tolerance.

The new Geranium can be compared to the cultivar Fisam (disclosed in U.S. Plant Pat. No. 8,327). Compared to plants of the cultivar Fisam, plants of the new Geranium are more compact, lighter in flower color, and have more peduncles but fewer flowers per peduncle.

The accompanying colored photograhs illustrate the overall appearance of the new cultivar, showing the colors as true as it is reasonably possible to obtain in colored reproductions of this type.

The first photograph comprises a top perspective view of a typical potted plant of 'Merifestival'.

The second photograph comprises a top perspective view of a typical flower of 'Merifestival'.

The third photograph comprises a top perspective view of typical leaves of 'Merifestival'.

Foliage and flower colors in the photograph may appear different from the actual colors due to light reflectance.

The cultivar 'Merifestival' has not been observed under all possible environmental conditions. The phenotype may vary somewhat with variations in environment such as temperature and light intensity, without, however, any variance in gentoype. The following observations, measurements and comparison describe plants grown in Wateringen, The Netherlands, under commercial practice in a glass-covered greenhouse with day temperatures of 20C and night temperatures of 18C and light levels of 450 W/m$^2$.

In the following description, color references are made to The Royal Horticultural Society Colour Chart except where general terms of ordinary dictionary significance are used.

Classification:

*Botanical.*—*Pelargonium×peltatum* cv. Merifestival.

*Commercial.*—Ivy Geranium.

Parentage:

*Male parent.*—Unidentified seedling selection.

*Female parent.*—Unidentified seedling selection.

Propagation:

*Type cutting.*—Terminal cuttings.

Time to initiate and develop roots: Summer: About 16 days at 20C. Winter: 16 to 20 days at 20C.

*Rooting habit.*—Vigorous, fast to root, freely branching.

Plant description:

*General appearance.*—Rounded and upright growth habit. Appropriate for 10.5 to 12 cm containers. About 12 weeks are required to produce a finished plant from an unrooted cutting.

*Growth rate.*—Moderate.

*Vigor.*—Moderate.

*Plant height.*—About 20 cm.

*Branching habit.*—Very freely branching with about 10 lateral branches per plant. Piniching (removal of terminal apices) is usually not required.

*Internode length.*—About 3 cm.

*Foliage description.*—Arrangement: Opposite. Shape: Generally reniform with cordate to overlapping lobes at the base. Aspect: Slightly undulating. Size:

Length: 3.5 to 5.5 cm. Width: 7 to 9.5 cm. Texture: Velvety, pubescent on abaxial surface. Margin: Lobed. Zonation: Very faint, about 1 cm in width and 2 to 3 cm from margin. Color: Abaxial surface: 137A/137B. Abaxial surface: 137B/137C. Zonation adaxial surface only: 147A. Venation pattern: Palmate. Petiole. Length: 6 to 8 cm. Diameter: 3 to 4 mm. Color: 143A/143B. Durability to rain, wind and stress conditions: Very good.

Following description:

*Flowering habit.*—Flowers arranged in umbels.

*Natural flowering season.*—Spring throughout summer.

*Flower longevity.*—Flowers last about 2.5 weeks on the plant. Flowers self-cleaning.

*Flowers borne.*—Flower buds develop in apical leaf axils. Umbels are displayed above the foliage.

*Umbels.*—Form: Rounded. Quantity of flowers per umbel: Usually 4 to 6. Diameter: 7 to 9 cm. Depth (height): 5 to 6 cm.

*Flowers.*—Form: Double. Shape: Rounded. Diameter: About 5 cm. Depth (height): About 2.5 cm. Quantity of petals and petaloids per flower: About 22.

*Petals.*—Shape: Obovate with rounded apex. Arrangement: Rosette, overlapping . Aspect: Flat. Size: Length: 2.6 to 3 cm. Width: About 1.5 cm. Texture: Satiny, smooth. Margin: Entire. Color: Opened flower, upper petals adaxial surface: 78C with dark purple stripes. Opened flower, upper petals, abaxial surface: 75C. Opened flower, lower petals, adaxial surface: 78C. Opened flower, lower petals, abaxial surface: 75C.

*Petaloids.*—Shape: Irregular, generally obovate with rounded or slightly incised apex. Arrangement: Rosette, overlapping . Size: Length: 1.5 to 2.5 cm. Width: About 1.5 cm. Texture: Satiny, smooth. Margin: Entire. Color: 75A.

*Peduncle (umbel stem).*—Angle: Semi-erect. Size: Length: 8 to 12 cm. Diameter: About 3 mm. Texture: Pubescent. Color: Medium to light green.

*Pedicel (individual flower stem).*—Angle: Between 45° to 90° from vertical. Size: Length: 2.5 to 2.8 cm. Diameter: 1 to 2 mm. Texture: Pubescent. Color: Medium to light green.

*Flower bud.*—Shape: Narrowly elliptic. Size: Length: About 1.4 cm. Diameter: About 7 mm. Color: Medium to light green.

*Sepals.*—Shape: Narrowly lanceolate with acuminate apex. Arrangement: Rosette. Quantity: 5 to 6. Size: Length: About 1.5 cm. Width: 3 to 6 mm. Texture: Smooth. Margin.—Entire. Color: Light green.

*Reproductive organs: Androecium: Stamen number:* 3 to 5. Anther shape: Elongated oval. Anther size: About 3 mm. Pollen color: 171B. Gynoecium: Pistil number: 1. Pistil length: About 1 cm. Stigma shape: Decurrent. Stigma color: 80C. Style length: About 5 mm. Style color: Light green.

Disease resistance: No fungal, bacterial noir viral problems observed under commercial conditions.

Seed developments: Seed production is very rarely observed.

It is claimed:

1. A new and distinct cultivar of Geranium plant named 'Merifestival', as illustrated and described.

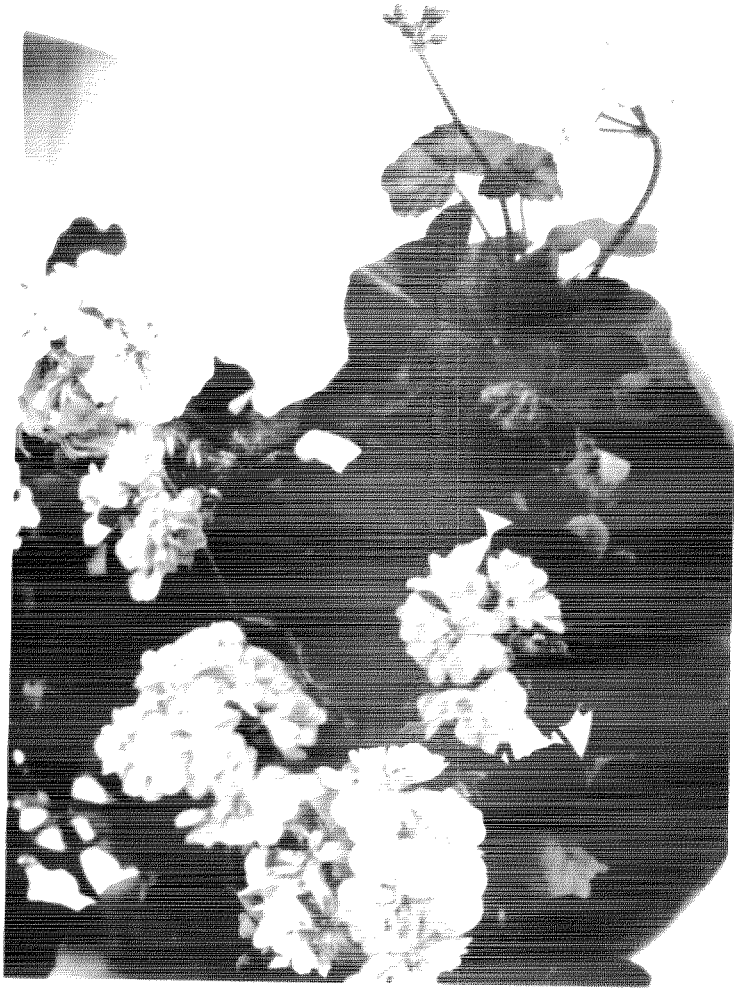

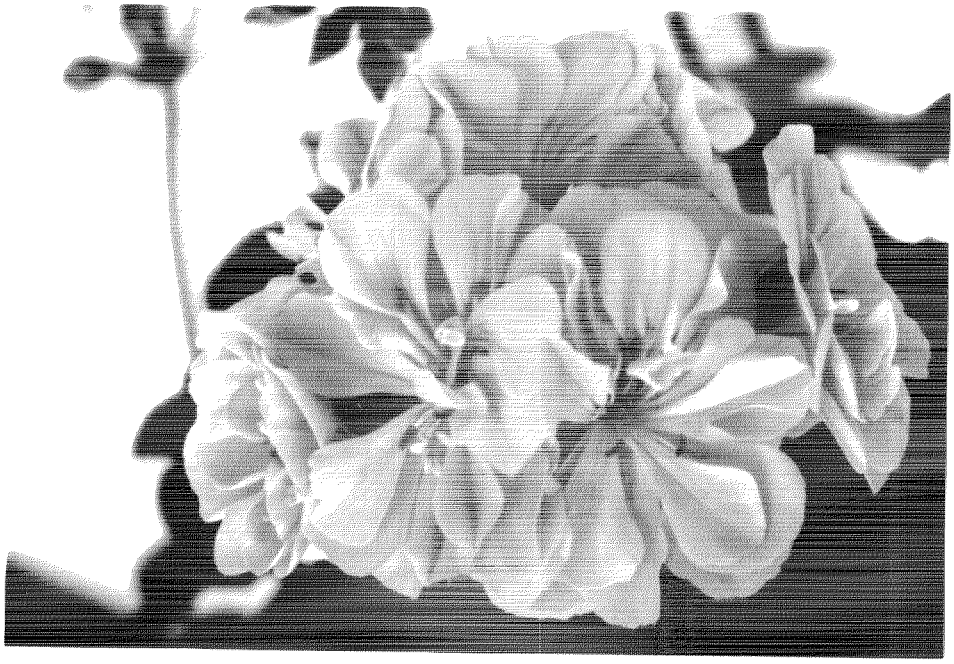
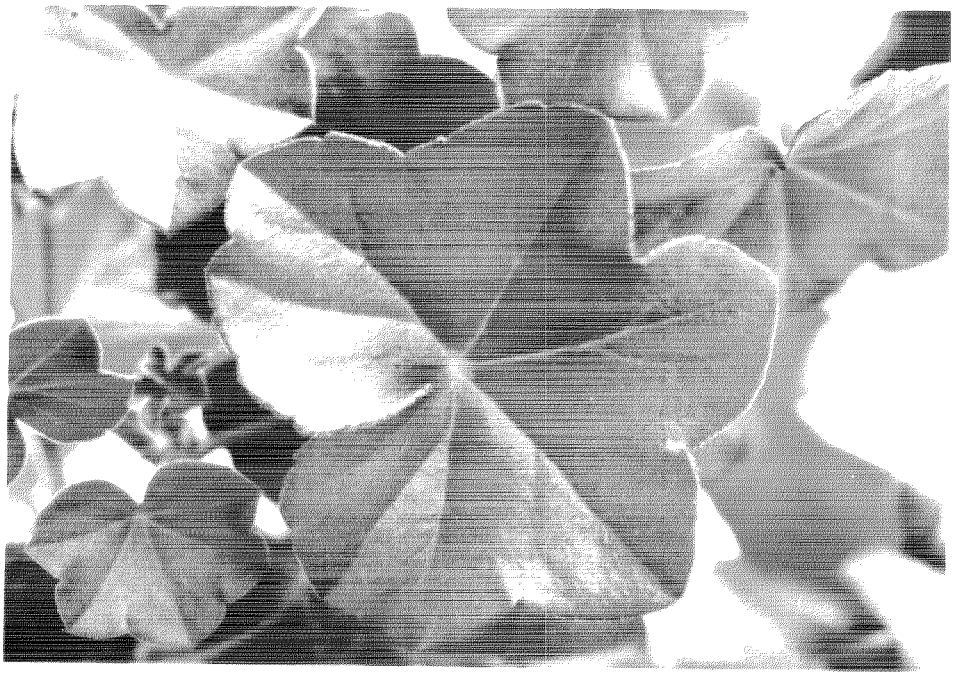

* * * * *